United States Patent
Kawashima et al.

(10) Patent No.: US 9,585,685 B2
(45) Date of Patent: Mar. 7, 2017

(54) ULTRASONIC TREATMENT INSTRUMENT

(71) Applicant: OLYMPUS CORPORATION, Hachioji-shi, Tokyo (JP)

(72) Inventors: Ko Kawashima, Musashino (JP); Minoru Kawasaki, Tokyo (JP); Kenichi Kimura, Hachioji (JP); Kazunori Taniguchi, Hamburg (DE)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/211,465

(22) Filed: Jul. 15, 2016

(65) Prior Publication Data

US 2016/0317179 A1    Nov. 3, 2016

Related U.S. Application Data

(63) Continuation of application No. PCT/JP2015/072131, filed on Aug. 4, 2015.

(30) Foreign Application Priority Data

Aug. 19, 2014 (JP) ................... 2014-166931

(51) Int. Cl.
  *A61B 17/32*     (2006.01)
  *A61B 18/00*     (2006.01)
  (Continued)

(52) U.S. Cl.
  CPC .... *A61B 17/320092* (2013.01); *A61B 17/295* (2013.01); *A61B 18/00* (2013.01);
  (Continued)

(58) Field of Classification Search
  CPC .......... A61B 17/295; A61B 17/320092; A61B 18/00; A61B 2017/00734; A61B 2017/2925; A61B 2018/00607; A61N 7/022
  See application file for complete search history.

(56) References Cited

U.S. PATENT DOCUMENTS

| | | | |
|---|---|---|---|
| 2013/0190759 A1* | 7/2013 | Waaler | H01M 2/1066 606/52 |
| 2014/0066910 A1 | 3/2014 | Nau, Jr. | |
| 2014/0207124 A1 | 7/2014 | Aldridge et al. | |

FOREIGN PATENT DOCUMENTS

| | | |
|---|---|---|
| JP | 2013-144108 A | 7/2013 |
| JP | 2013-150803 A | 8/2013 |
| WO | 2009/073608 A1 | 6/2009 |

OTHER PUBLICATIONS

Sep. 15, 2015 International Search Report issued in Patent Application No. PCT/JP2015/072131.

* cited by examiner

*Primary Examiner* — Daniel Fowler
(74) *Attorney, Agent, or Firm* — Oliff PLC

(57) ABSTRACT

In an ultrasonic treatment instrument, a vibration generation section is connected to a probe from a proximal direction side in an inside of a case by coupling a drive assembly integrally and detachably to a handle assembly. An opposite extended portion is extended from the case in a state where the opposite extended portion is opposed to the movable handle on the proximal direction side with respect to the movable handle and a space between the opposite extended portion and the movable handle can be opened and closed, when the drive assembly is coupled to the handle assembly. A battery is located in the opposite extended portion, when the drive assembly is coupled to the handle assembly.

7 Claims, 9 Drawing Sheets

(51) Int. Cl.
*A61B 17/295* (2006.01)
*A61N 7/02* (2006.01)
A61B 17/00 (2006.01)
A61B 17/29 (2006.01)

(52) U.S. Cl.
CPC .... *A61N 7/022* (2013.01); *A61B 2017/00734* (2013.01); *A61B 2017/2925* (2013.01); *A61B 2018/00607* (2013.01)

ULTRASONIC TREATMENT INSTRUMENT

CROSS-REFERENCE TO RELATED APPLICATIONS

This is a Continuation application of PCT Application No. PCT/JP2015/072131, filed Aug. 4, 2015 and based upon and claiming the benefit of priority from prior Japanese Patent Application No. 2014-166931, filed Aug. 19, 2014, the entire contents of which are incorporated herein by reference.

BACKGROUND OF THE INVENTION

1. Field of the Invention

The present invention relates to an ultrasonic treatment instrument for treating a treated target with an ultrasonic vibration generated in a vibration generation section, using an electric power output from a battery.

2. Description of the Related Art

An example in International Publication No. 2009/073608 discloses an ultrasonic treatment instrument which generates an ultrasonic vibration by an ultrasonic transducer using an electric power output from a battery. In this ultrasonic treatment instrument, the ultrasonic vibration generated in the ultrasonic transducer is transmitted from a proximal portion to a distal portion of a probe extended along a longitudinal axis. A target for treatment, such as living tissue, etc., is treated at the distal portion of the probe, using the ultrasonic vibration. The proximal portion of the probe is located inside of a case of a handle assembly, and a transducer unit including an ultrasonic transducer is detachably coupled to the case from the proximal direction side. Since the transducer unit is coupled to the case, a vibration generation section including an ultrasonic transducer is connected to the probe from the proximal direction side in the inside of the case. Furthermore, the handle assembly includes a stationary handle extended from the case toward a direction intersecting the longitudinal axis, and a movable handle which can close and open with respect to the stationary handle. A housing cavity is formed inside of the stationary handle, and the battery is detachably attached to the stationary handle in the housing cavity.

In an ultrasonic treatment instrument of another example in International Publication No. 2009/073608, a drive assembly including a vibration generation section, a battery, and a drive control section which controls a driving of the vibration generation section using an electric power from the battery are provided. In this ultrasonic treatment instrument, the driving assembly is coupled integrally with and detachably to the handle assembly from the proximal direction side. By coupling the drive assembly to the handle assembly, the vibration generation section is connected to the proximal direction side of the probe in the inside of the case.

BRIEF SUMMARY OF THE INVENTION

According to one aspect of the invention, an ultrasonic treatment instrument includes that: a probe which has a distal portion and a proximal portion, is extended along a longitudinal axis C, and is configured to transmit an ultrasonic vibration; a handle assembly including a case inside which the proximal portion of the probe is located, and a movable handle which is extended from the case in a direction intersecting the longitudinal axis and which is movably attached to the case; a drive assembly including a vibration generation section which is configured to generate the ultrasonic vibration by being driven, a battery which is configured to output an electric power, and a drive control section which is configured to control a drive of the vibration generation section using the electric power from the battery, the vibration generation section being connected to the probe from a proximal direction side in an inside of the case by coupling the drive assembly integrally and detachably to the handle assembly; and an opposite extended portion which is extended from the case in a state where the opposite extended portion is opposed to the movable handle on the proximal direction side with respect to the movable handle when the drive assembly is coupled to the handle assembly, and in which the battery is located, a space between the opposite extended portion and the movable handle being able to be opened and closed.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION (First Embodiment)

The first embodiment of the present invention will be explained with reference to FIG. 1 to FIG. 4.

Figure 1:
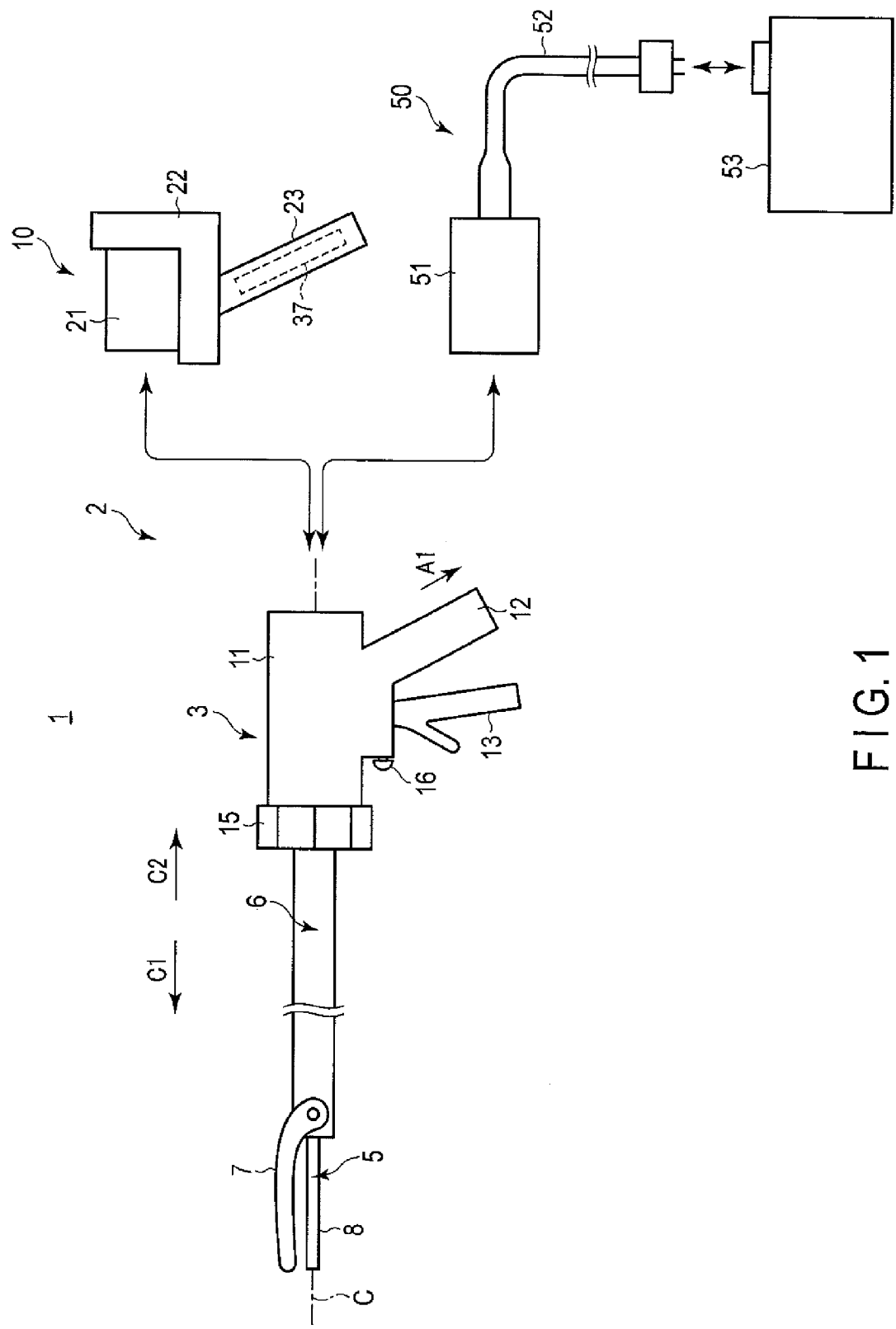
FIG. 1 is a schematic diagram illustrating the ultrasonic system according to the first embodiment.

FIG. 1 shows the ultrasonic treatment system 1 according to the present embodiment. As shown in FIG. 1, the ultrasonic treatment system 1 includes a handle assembly (handle unit) 3 and a probe (ultrasonic probe) 5. The probe 5 has a distal portion and a proximal portion, and is extended along the longitudinal axis C. In the present embodiment, the longitudinal axis C is a central axis of the probe 5. Herein, one of two directions parallel to the longitudinal axis C is defined as a distal direction (indicated by arrow C1 in FIG. 1), and the other direction opposite to the distal direction is defined as a proximal direction (indicated by arrow C2 in FIG. 1).

The handle assembly (handle unit) 3 includes a case 11 in which a space is formed inside, and a stationary handle 12 extended from the case 11 toward one direction (the direction indicated by arrow A1 in FIG. 1) intersecting the longitudinal axis C. In the present embodiment, the case 11 is extended approximately coaxially with the longitudinal axis C. The stationary handle 12 is formed integrated with the case 11 and fixed to the case 11.

The held assembly 3 includes a movable handle 13 which is pivotably (movably) attached to the case 11. The movable handle 13 is extended from the case 11 toward a direction intersecting the longitudinal axis C. The movable handle 13 is located on the distal direction side with respect to the stationary handle 12, and the handle assembly 3 is formed in a pistol shape. The movable handle 13 is located on the same side as the stationary handle 12 with respect to the longitudinal axis C (probe 5). Because of the above-described configuration, the stationary handle 12 is extended from the case 11 in a state where the stationary handle 12 is opposed to the movable handle 13 on the proximal direction side with respect to the movable handle 13. Upon the movable handle 13 pivoting with respect to the case 11, the movable handle 13 is closed or opened with respect to the stationary handle 12. In other words, the space between the movable handle 13 and the stationary handle 12 can be closed and opened.

The handle assembly 3 includes a rotating operation knob 15 which is a rotating operation section that is coupled on the distal direction side of the case 11. The rotating operation knob 15 is rotatable with respect to the case 11 around the longitudinal axis C. An energy operation input button 16, which is an energy operation input section and to which an energy operation is input, is provided in the handle assembly 3.

A sheath 6 is coupled to the distal direction side of the rotating operation knob 15. The sheath 6 has a distal portion and a proximal portion, and the proximal portion of the sheath 6 is located inside of the case 11. The sheath 6 is extended along the longitudinal axis C, and the sheath is approximately coaxial with the longitudinal axis C in the present embodiment. The jaw (gripping member) 7 is pivotably attached at the distal portion of the sheath 6. By opening or closing the movable handle 13 with respect to the stationary handle 12, the movable portion (not shown) in the inside of the sheath 6 moves along the longitudinal axis C. This causes the jaw 7 to pivot with respect to the sheath 6.

The probe 5 is extended and passes through the inside of the sheath 6. A probe treatment section 8 which performs treatment to a target for treatment, such as living tissue, etc. is formed in the distal portion of the probe 5. The probe 5 is inserted through the sheath 6 in a state where the probe treatment section 8 is projected from the sheath 6 toward the distal direction side. Upon the jaw 7 rotating with respect to the sheath 6, the jaw 7 is closed or opened with respect to the probe treatment section 8. The proximal portion of the probe 5 is located inside of the case 11. The probe 5, the sheath 6, and the jaw 7 are rotatable about the longitudinal axis C with respect to the case 11, integral with the rotating operation knob 15.

The drive assembly (drive unit) 10 is integrally and detachably coupled to the handle assembly 3. In other words, the drive assembly 10 is integrally coupled with the handle assembly 3. In the present embodiment, the drive assembly 10 is coupled to the handle assembly 3 on the proximal direction side of the handle assembly 3. The ultrasonic treatment instrument 2 can be assembled by coupling the drive assembly 10 to the handle assembly 3.

Figure 2:
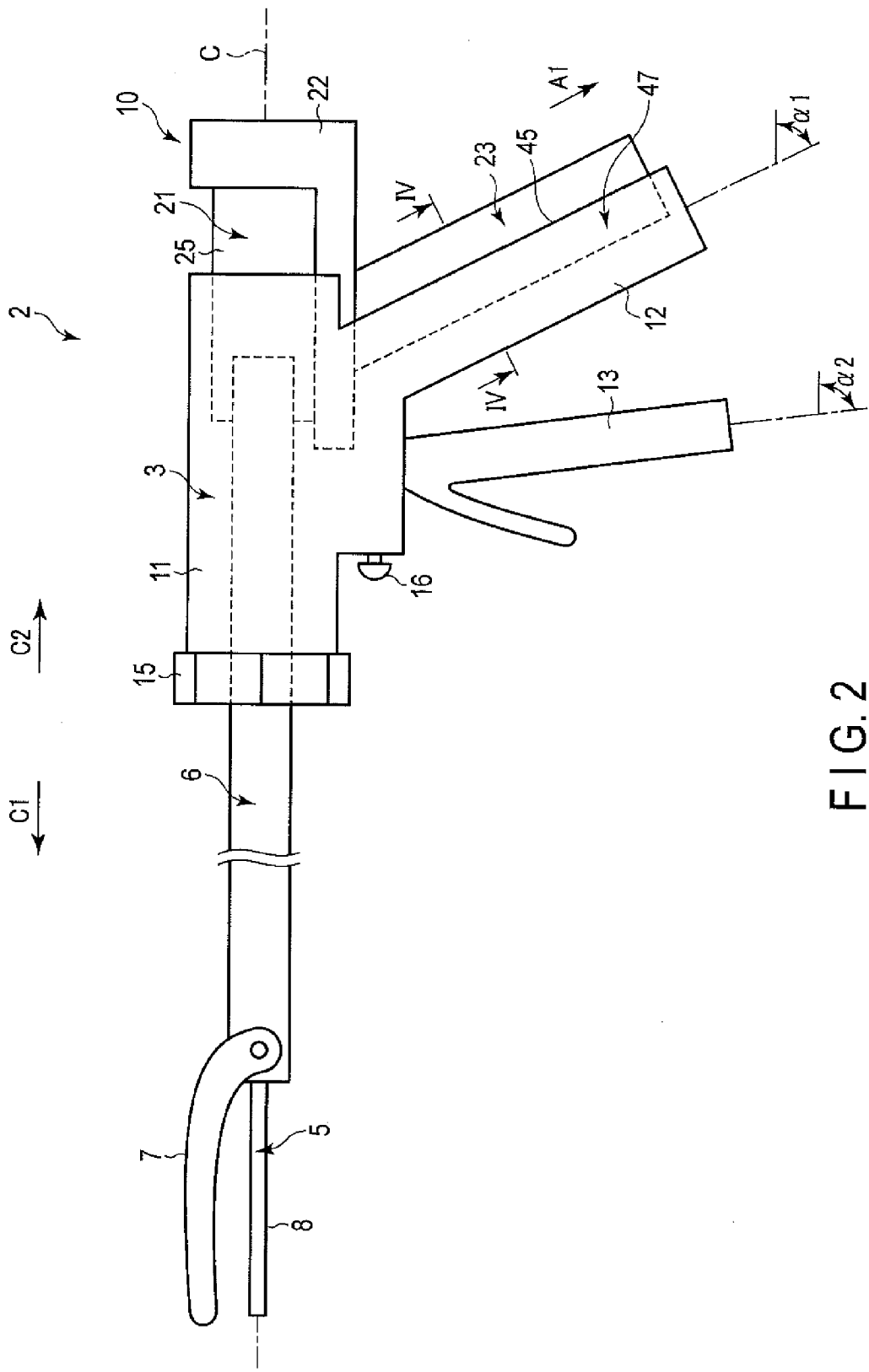
FIG. 2 is a schematic diagram illustrating the ultrasonic treatment instrument in which the drive assembly is coupled to the handle assembly according to the first embodiment.

FIG. 2 is a schematic diagram illustrating the ultrasonic treatment instrument 2 in which the drive assembly 10 is coupled to the handle assembly 3. As shown in FIGS. 1 and 2, the drive assembly 10 includes a transducer unit 21 and a supporting member 22 which supports the vibrator unit 21. Since the drive assembly 10 is coupled to the handle assembly 3, the transducer unit 21 is coupled to the case 11 on the proximal direction side of the case 11. The drive assembly 10 includes a battery unit 23. The battery unit 23 is located on the opposite side of the transducer unit 21 with respect to the supporting member 22. Since the drive assembly 10 is coupled to the held assembly 3, the battery unit 23 is coupled to the stationary handle 12 from the proximal direction side. Furthermore, in the ultrasonic treatment tool 2 in which the drive assembly 10 is coupled to the handle assembly 3, the battery unit 23 is located on the same side as the movable handle 12 and the stationary handle 12 with respect to the longitudinal axis C (probe 5).

The battery unit 23 may be formed in integration with the transducer unit 21 and the supporting member 22, and may be coupled detachably to the supporting member 22. In the configuration in which the battery unit 23 is detachable from the supporting member 22, the battery unit 23 is coupled to the supporting member 22, and then the drive assembly 10 is integrally coupled to the handle assembly 3 after assembling the drive assembly 10. FIG. 2 shows a state where the movable handle 13 is most open with respect to the stationary handle 12.

Figure 3:
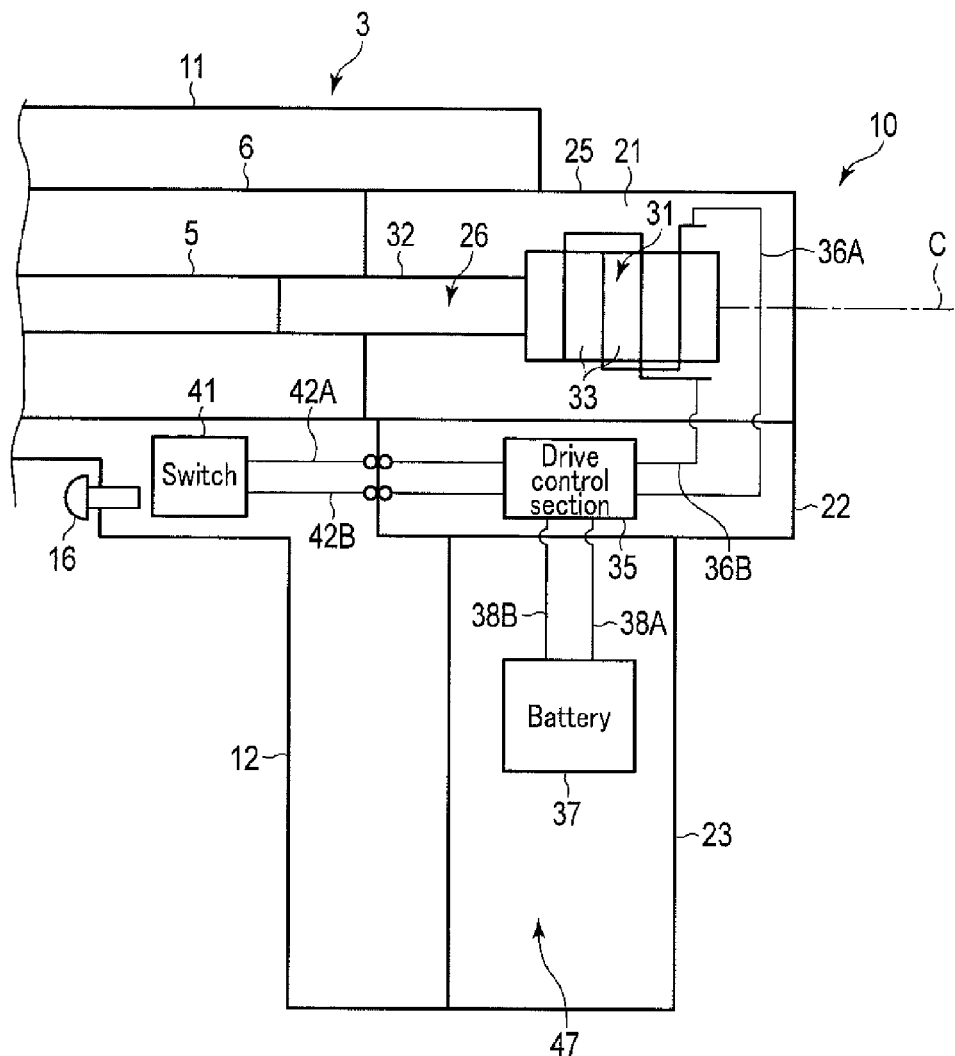
FIG. 3 is a schematic diagram illustrating the configuration of the handle assembly and the drive assembly according to the first embodiment.

FIG. 3 shows the configuration of the handle assembly 3 and the drive assembly 10. As shown in FIGS. 2 and 3, the transducer unit 21 of the drive assembly 10 includes a transducer case 25 in which a space is formed therein, and a vibration generation section 26 which is provided inside the vibrator case 25. The vibration generation section 26 includes an ultrasonic transducer 31 generating an ultrasonic vibration as a result of being supplied with an alternating current (electric power), and a column-shaped horn member 32 to which the ultrasonic vibrator 31 is attached. A piezoelectric element 33 (a plurality of piezoelectric elements in the case of the present embodiment) configured to convert an alternating current (electric power) into ultrasonic vibration is provided in the ultrasonic transducer 31.

The transducer case 25 is inserted inside of the case 11 from the proximal direction side by coupling the drive assembly 10 to the handle assembly 3. The vibrator case 25 is thus coupled to the sheath 6 in the inside of the case 11 from the proximal direction side. In the present embodiment, the transducer case 25 is approximately coaxial with the longitudinal axis C. The transducer case 25 and the sheath 6 are coupled in such a manner that they can rotate about the longitudinal axis C with respect to each other. Thus, the transducer case 25 does not rotate with the rotating operation knob 15, and it is fixed to the case 11.

Since the drive assembly 10 is coupled to the handle assembly 3, the vibration generation section 26 is inserted inside of the case 11 from the proximal direction side. The vibration generation section 26 is then connected to the probe 5 from the proximal direction side in the inside of the case 11. For example, the vibration generation section 26 is connected to the probe 5 by threadedly engaging the distal portion of the horn member 32 with the proximal end of the probe 5. In the present embodiment, the vibration generation section 26 is approximately coaxial with the longitudinal axis C. The vibration generation section 26 is supported by the transducer case 25 so as to be rotatable about the longitudinal axis C. Thus, by rotating the rotating operation knob 15, the vibration generation section 26 is rotatable about the longitudinal axis C with respect to the transducer case 25, in accordance with the rotating operation knob 15, and the probe 5.

In the drive assembly 10, the transducer case 25 is fixed to the supporting member 22. In the drive assembly 10, the battery unit 23 is fixed to the supporting member 22. Thus, in the ultrasonic treatment instrument 2 in which the drive assembly 10 is coupled to the handle assembly 3, the supporting member 22 and the battery unit 23 are fixed with respect to the case 11, and do not rotate with the rotating operation knob 15.

As shown in FIG. 3, a drive control section 35 configured to control the drive of the vibration generation section 26 (ultrasonic transducer 31) is formed in the supporting member 22. The drive control section 35 is electrically connected to the ultrasonic transducer 31 (vibration generation section 26) via the electric wiring 36A and 36B. The drive control section 35 consists of processors, for example, an electronic circuit (a detector circuit, a control circuit, a drive circuit, a conversion circuit, etc.) or a central processing unit (CPU) including those electronic circuits, an application specific integrated circuit (ASIC), etc. Furthermore, a memory (memory medium) storing information about the characteristics of the ultrasonic treatment instrument 2 and processing programs, etc. is provided in the drive control section 35.

A battery 37, which is an electric power source, and a protection circuit (not shown), which performs control to protect the battery 37 from overcharging, over-discharging, and overcurrent, etc. are provided in the battery unit 23. In the drive assembly 20, the battery 37 is electrically connected to the drive control section 35 via the electric wiring 38A and 38B. The direct current (electric power) output from the battery 37 is supplied to the drive control section 35 via electric wiring 38A and 38B.

A switch 41 is provided inside of the handle assembly 3. The switch 41 is arranged at a location so that it can be pressed down by the energy operation input button 16. The switch 41 is switched between the closed state and the opened state in accordance with an input of an energy operation at the energy operation input button 16. For example, the switch 41 is switched from the opened state to the closed state by inputting energy operation (by pressing down the energy operation input button 16). It should be noted that more than one energy operation input button 16 and the switch 41 may be provided, as needed.

In the ultrasonic treatment instrument 2 in which the drive assembly 10 is coupled to the handle assembly 3, the switch 41 is electrically connected to the drive control section 35 of the drive assembly 10 via the electric wiring 42A and 42B. In the ultrasonic treatment instrument 2, the drive control section 35 detects the opened or closed state of the switch 41 by measuring a current flowing in the electric wiring 42A and 42B, for example. Thus, an energy operation input at the energy operation input button 16 is detected by the drive control section 35. When the drive assembly 10 is detached from the handle assembly 3, the electric connection between the switch 41 and the drive control section 35 is cut off.

When an energy operation input is detected, the drive control section 35 converts a direct current supplied from the battery 37 into the alternating current. Then, the converted alternating current is supplied to the ultrasonic transducer 31 (vibration generation section 26) via the electronic wiring 36A and 36B, and the vibration generation section 26 (ultrasonic vibrator 31) is driven. Thus, the alternating current supplied to the ultrasonic transducer 31 is converted into the ultrasonic vibration, and the ultrasonic vibration is generated in the ultrasonic transducer 31.

The ultrasonic vibration generated in the ultrasonic vibrator 31 is transmitted to the probe 5 via the horn member 32. The horn member 32 is provided with a cross-sectional area changing portion (not shown) in which the area of the cross section perpendicular to the longitudinal axis C reduces toward the distal direction, and the amplitude of the ultrasonic vibration is increased at the cross-sectional area changing portion. The ultrasonic vibration is transmitted from the proximal portion (proximal direction) toward the distal portion (distal direction) in the probe 5. Then, the ultrasonic vibration is transmitted to the probe treatment section 8, and the probe treatment section 8 performs treatment on a treated target using the transmitted ultrasonic vibration. When the probe 5 is in a state of transmitting ultrasonic vibration, the probe 5 (horn member 32) longitudinally vibrates in a state in which a vibrating direction is parallel to the longitudinal axis C.

Figure 4:
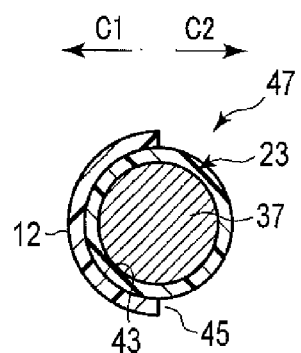
FIG. 4 is a cross-sectional view taken along line IV-IV indicated in FIG. 2.

FIG. 4 is a cross-sectional view taken along line IV-IV in FIG. 2. As shown in FIG. 4, a housing cavity 43 is formed inside of the stationary handle 12. The housing cavity 43 is formed along a direction in which the stationary handle 12 is extended from the case 11 (the direction indicated by arrow A1 in FIGS. 1 and 2). The housing cavity 43 opens at an opening 45 toward the proximal direction side. Accordingly, in the cross section perpendicular to a direction in which the stationary handle 12 is extended, the stationary handle 12 is approximately U-shaped.

Since the drive assembly 10 is coupled to the handle assembly 3, the battery unit 23 is inserted into the housing cavity 43 from the opening 45. Thus, in the ultrasonic treatment instrument 2 in which the drive assembly 10 is coupled to the handle assembly 3, the battery unit 23 including the battery 37 is stored in the housing cavity 43 of the stationary handle 12.

Furthermore, in the ultrasonic treatment instrument 2, the stationary handle 12 and the battery unit 23 form the opposite extended portion 47. The opposite extended portion 47 is extended from the case 11 toward an extension direction of the stationary handle 12 (i.e., one direction intersecting the longitudinal axis C). The relative position of the opposite extended portion 47 with respect to the case 11 in the ultrasonic treatment instrument 2 is approximately the same as the relative position of the stationary handle 12 with respect to the case 11 in the handle assembly 3. Thus, the opposite extended portion 47 is extended from the case 11 in a state where the opposite extended portion 47 is opposed to the movable handle 13 on the proximal direction side with respect to the movable handle 13. Furthermore, the space between the opposite extended portion 47 and the movable handle 13 can be closed and opened.

As shown in FIG. 2, in the present embodiment, the angle α1 is an acute angle between the direction in which the opposite extended portion 47 is extended from the case 11 (i.e., the direction in which the stationary handle 12 is extended) and the proximal direction. When the movable handle 13 is most open with respect to the opposite extended portion 47 (stationary handle 12), the angle α2 is an acute angle between the direction in which the movable handle 12 is extended from the case 11 and the proximal direction.

As shown in FIG. 1, when the charge of the battery 37 of the battery unit 23 runs out, a wired transducer unit 50 may be detachably coupled to the handle assembly 3 from the proximal direction side, instead of the drive assembly 10. In other words, the wired vibrator unit 50 is prepared as an auxiliary means when the charge of the battery 37 runs out, and the wired transducer unit 50 is configured to be coupled to the handle assembly 3. The wired transducer unit 50 includes a transducer case 51. Similar to the transducer unit 21 of the drive assembly 10, a wired vibration generation section (not shown) including piezoelectric elements (not shown) in the inside of the transducer case 51 is provided. Since the wired vibrator unit 50 is coupled to the handle assembly 3, a wired vibration generation section (vibration generation section) is connected to the probe 5 from the proximal direction side in the inside of the case 11.

In the wired transducer unit 50, one end of the cable 52 is connected to the transducer case 51. The other end of the cable 52 is connectible to the energy source unit 53. The energy source unit 53 is an electric power generator including an electric power source and a processor, such as a CPU or ASIC. The energy source unit 53 is capable of outputting alternating current (electric power). The alternating current output from the energy source unit 53 is supplied to a wired vibration generation section of the wired transducer unit 50 via electric wiring (not shown) inside of the cable 52. Thus, similar to the vibration generation section 26 of the drive assembly 10, the ultrasonic vibration is generated in the wired vibration generation section. Furthermore, the generated ultrasonic vibration is transmitted to the probe treatment section 8 via the probe 5.

Since the wired transducer unit 50 is coupled to the handle assembly 3, and the cable 52 is connected to the energy source unit 53, the switch 41 of the handle assembly 3 is electrically connected to the energy source unit 53 via electric wiring (not shown) extended through the wired transducer unit 50. Thus, the energy source unit 53 detects the opened or closed state of the switch 41 by measuring a current flowing in the electric wiring, and an energy operation input by the energy operation input button 16 is detected. When the input of the energy operation is detected, an alternating current is supplied to the vibration generation section of the wired transducer unit 50.

Next, the function and advantageous effects of the ultrasonic treatment system 1 and the ultrasonic treatment instrument 2 are described. In the present embodiment, treatment is performed mainly using the ultrasonic treatment instrument 2 in which the drive assembly 10 is coupled to the handle assembly 3. When treatment is performed, first the drive assembly 10 is coupled to the handle assembly 3 to which the probe 5 and the sheath 6 are attached. Thus, in the inside of the case 11, the transducer case 25 is coupled on the proximal side of the sheath 6, and the vibration generation section 26 is connected on the proximal direction side of the probe 5. Furthermore, the battery unit 23 is inserted into the housing cavity 43 from the opening 45, and is stored in the housing cavity 43 of the stationary handle 12. Thus, the stationary handle 12 and the battery unit 23 form the opposite extended portion 47. Furthermore, the switch 41 of the handle assembly 3 is electrically connected to the drive control section 35 of the drive assembly 10.

Accordingly, by coupling the drive assembly 10 to the handle assembly 3, the vibration generation section 26 (ultrasonic transducer 31), the drive control section 35, and the battery 37 are integrally attached to the handle assembly 3. In other words, the ultrasonic treatment instrument 2 including the vibration generation section 26 (ultrasonic transducer 31), the drive control section 35, and the battery 37 can be assembled only by coupling the drive assembly 10 to the handle assembly 3. Thus, simplification of the structure for assembling the ultrasonic treatment instrument 2 can be realized, and the ultrasonic treatment instrument 2 can be easily assembled.

Upon assembling the ultrasonic treatment instrument 2, the probe 5, the sheath 6, and the jaw 7 are inserted into the body cavity. Then, a target for treatment, such as living tissue, etc., is arranged between the probe treatment section 8 and the jaw 7. Furthermore, by closing the movable handle 13 with respect to the opposite extended portion 47 (stationary handle 12), the jaw 7 is closed with respect to the probe treatment section 8, and the treated target is gripped by the probe treatment section 8 and the jaw 7.

While the target for treatment is being gripped, the switch 41 is closed by inputting an energy operation with the energy operation input button 16, and the energy operation input is detected by the drive operation section 35. Upon detecting the energy operation, an alternating current is supplied to the vibration generation section 26 (ultrasonic transducer 31) from the drive control section 35 by using the direct current supplied from the battery 37. Upon being supplied with the alternative electric power, the vibration generation section 26 is driven, and the ultrasonic vibration is generated at in ultrasonic transducer 31. The generated ultrasonic vibration is transmitted from the proximal direction toward the distal direction in the probe 5, and is then transmitted to the probe treatment section 8. As a result, the probe 5 vibrates in a longitudinal direction. The longitudinal vibration of the probe treatment section 8 while the target for treatment is being gripped between the probe treatment tool 8 and the jaw 7 causes frictional heat between the probe treatment section 8 and the treated target. The frictional heat causes coagulation and incision of the target for treatment at the same time.

At the time of treatment, the operator holds the movable handle 13 and the opposite extended portion 47 (stationary handle 12). In the ultrasonic treatment instrument 2 of the present embodiment, the vibration generation section 26 having a heavy weight is arranged on the proximal direction side of the case 11. In other words, if the direction in which the opposite extended direction 47 (stationary handle 12) is extended from the case 11 (the direction indicated by arrow A1 in FIG. 1) is defined as a handle extended direction, the vibration generation section 26 is arranged on the side opposite to the handle extended direction with respect to the movable handle 13 and the opposite extended section 47 which are held by the operator at the time of treatment. However, in the present embodiment, the battery 37, which has a weight similar to the weight of the vibration generation section 26, is arranged in the housing cavity 43 in the inside of the stationary handle 12. In other words, the battery 37 is arranged in the opposite extended portion 47 which is held by the surgeon at the time of treatment.

In the ultrasonic treatment instrument 2 of the present embodiment, by arranging heavy vibration generation section 26 and the battery 37 in the above-described manner, the weight would not be excessively heavy on the portion opposite to the handle extended direction with respect to the movable handle 13 and the opposite extended section 47, which are held by the operator at the time of treatment. In other words, the center of gravity of the ultrasonic treatment instrument 2 is located closer to the movable handle 13 and the opposite extended portion 47 with respect to the longitudinal axis C. Thus, the center of gravity can be well balanced in the ultrasonic treatment instrument 2. Thus, at the time of treatment, the operator can easily adjust the positions of the jaw 7 and the probe treatment section 8, thereby securing operability at the time of treatment.

In the ultrasonic treatment instrument 2, the angle α1 is an acute angle between the direction in which the opposite extended portion 47 is extended from the case 11 (i.e., the direction in which the stationary handle 12 is extended) and the proximal direction. When the movable handle 13 is most open with respect to the opposite extended portion 47, the angle α2 is an acute angle between the direction in which the movable handle 12 is extended from the case 11 and the proximal direction. Thus, the operator can easily hold the opposite extended portion 47 and the movable handle at the time of treatment, and the operability can be further improved.

When the treatment is finished, the drive assembly 10 is integrally detached from the handle assembly 3. At this time, the transducer case 25 is detached from the sheath 6, and the vibration generation section 26 is separated from the probe 5. The battery unit 23 is also detached from the stationary handle 12. Then, the handle assembly 3, the probe 5, the sheath 6, and the jaw 7 are discarded. On the other hand, the drive assembly 10, including expensive piezoelectric elements 33 (vibration generation section 26) and the battery 37 (battery unit 23), are sterilized for reuse. Thus, it is possible to separate the reusable members integrally from the members to be discarded by detaching the drive assembly 10 from the handle assembly 3.

Furthermore, when the charge of the battery 37 indicates zero at the time of treatment and the battery 37 does not output the electric power any more, the drive assembly 10 is detached from the handle assembly 3, and the wired transducer unit 50 is coupled to the handle assembly 3 instead. Then, the cable 52 of the wired transducer unit 50 is connected to the energy source unit 53. Under these circumstances, an alternating current is supplied from the energy source unit 53 to the wired vibration generation section (not shown) of the wired transducer unit 50 by inputting an energy operation with the energy operation input button 16, and the ultrasonic vibration is generated. The generated ultrasonic vibration is then transmitted to the probe treatment section 8 via the probe 5. Thus, even when the charge of the battery 37 indicates zero, treatment similar to the treatment performed by the ultrasonic treatment instrument 2 in which the drive assembly 10 is coupled to the handle assembly 3 can be carried out using the wired transducer unit 50 and the energy source unit 53.

(Modifications)

Figure 5:
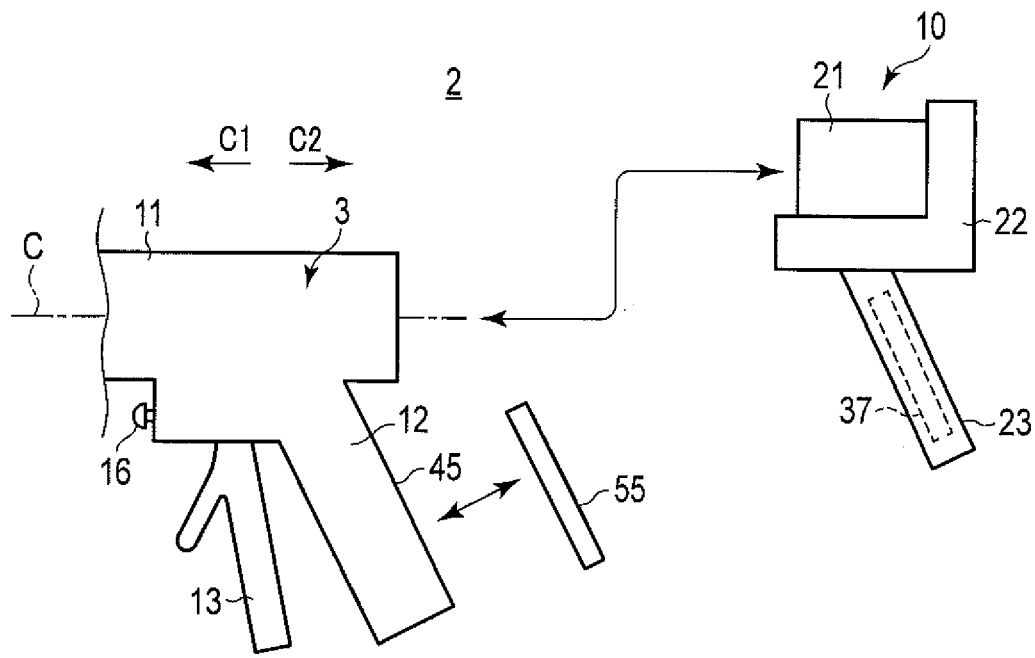
FIG. 5 is a schematic diagram of the configuration of the handle assembly and the drive assembly according to the first modification.
Figure 6:
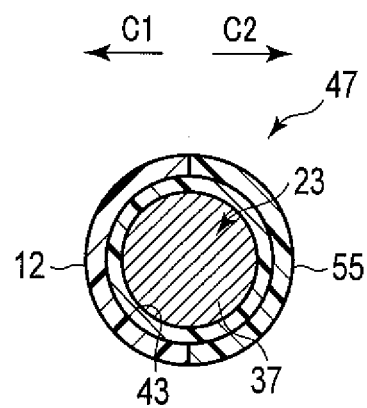
FIG. 6 is a schematic cross-sectional view illustrating the opposite extended portion according to the first modification in the cross section perpendicular to the extended direction.

In the first modification shown in FIGS. 5 and 6, the handle assembly 3 includes a lid member detachably attached to the stationary handle 12. The lid member 55 is attached to the stationary handle 12 from the proximal direction side. In the present modification, the opening 45 of the housing cavity 43 of the stationary handle 12 is covered by the lid member 55 which is attached to the stationary handle 12.

In the present modification, after coupling the drive assembly 10 to the handle assembly 3 to which the probe 5 and the sheath 6 are attached, the lid member 55 is attached to the stationary handle 12. Thus, in the opposite extended portion 47, the battery unit 23 including the battery 37 would not be exposed to the exterior.

Figure 7:
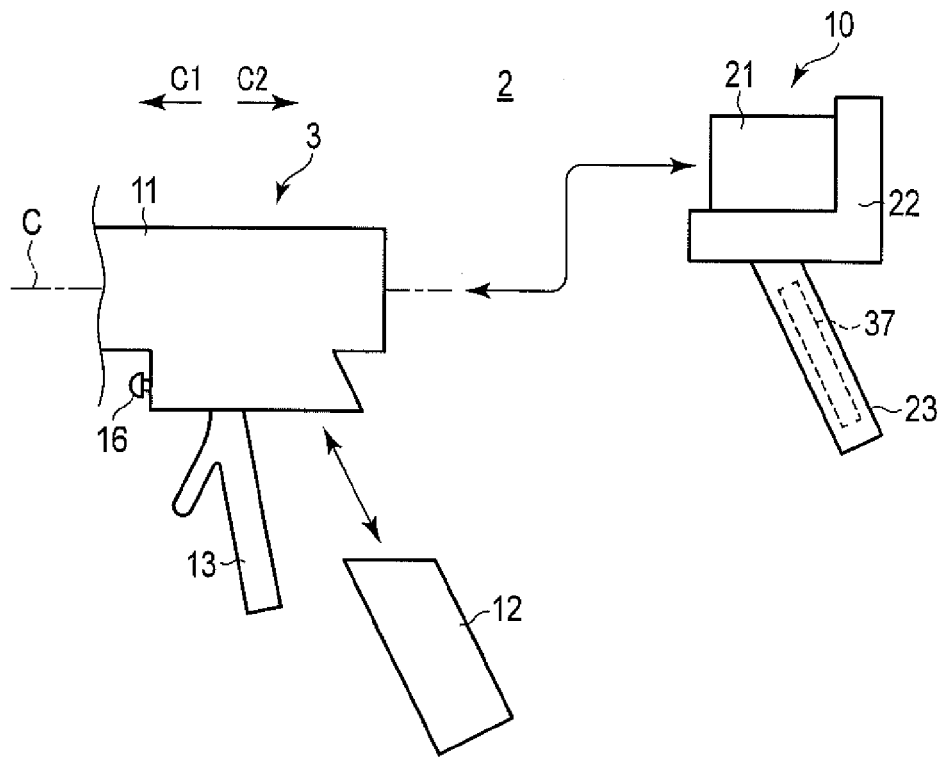
FIG. 7 is a schematic diagram illustrating the configuration of the handle assembly and the drive assembly according to the second modification in a state where the drive assembly is separated from the handle assembly.
Figure 8:
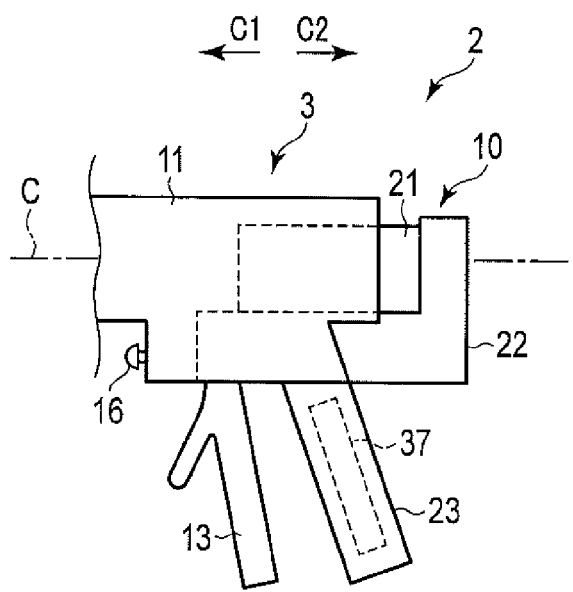
FIG. 8 is a schematic diagram illustrating the configuration of the handle assembly and the drive assembly according to the second modification in the state where the drive assembly is coupled to the handle assembly.

Furthermore, in the handle assembly 3 according to the second modification illustrated in FIGS. 7 and 8, the stationary handle 12 is detachable from the case 11. In other words, the stationary handle 12 is detachably fixed to the case 11. In the present modification, the drive assembly 10 is coupled to the handle assembly 3 while the stationary handle 12 is detached from the case 11. Thus, the battery unit 23 forms the opposite extended portion 47 when the drive assembly 10 is coupled to the handle assembly 3. In other words, a part of the drive assembly 10 forms the opposite extended portion 47 where the battery 37 is located.

In the present modification, in a case of performing treatment using the wired transducer unit 50 and the energy source unit 53 instead of the drive assembly 10, the stationary handle 12 is fixed to the case 11 in the handle assembly 3.

Figure 9:
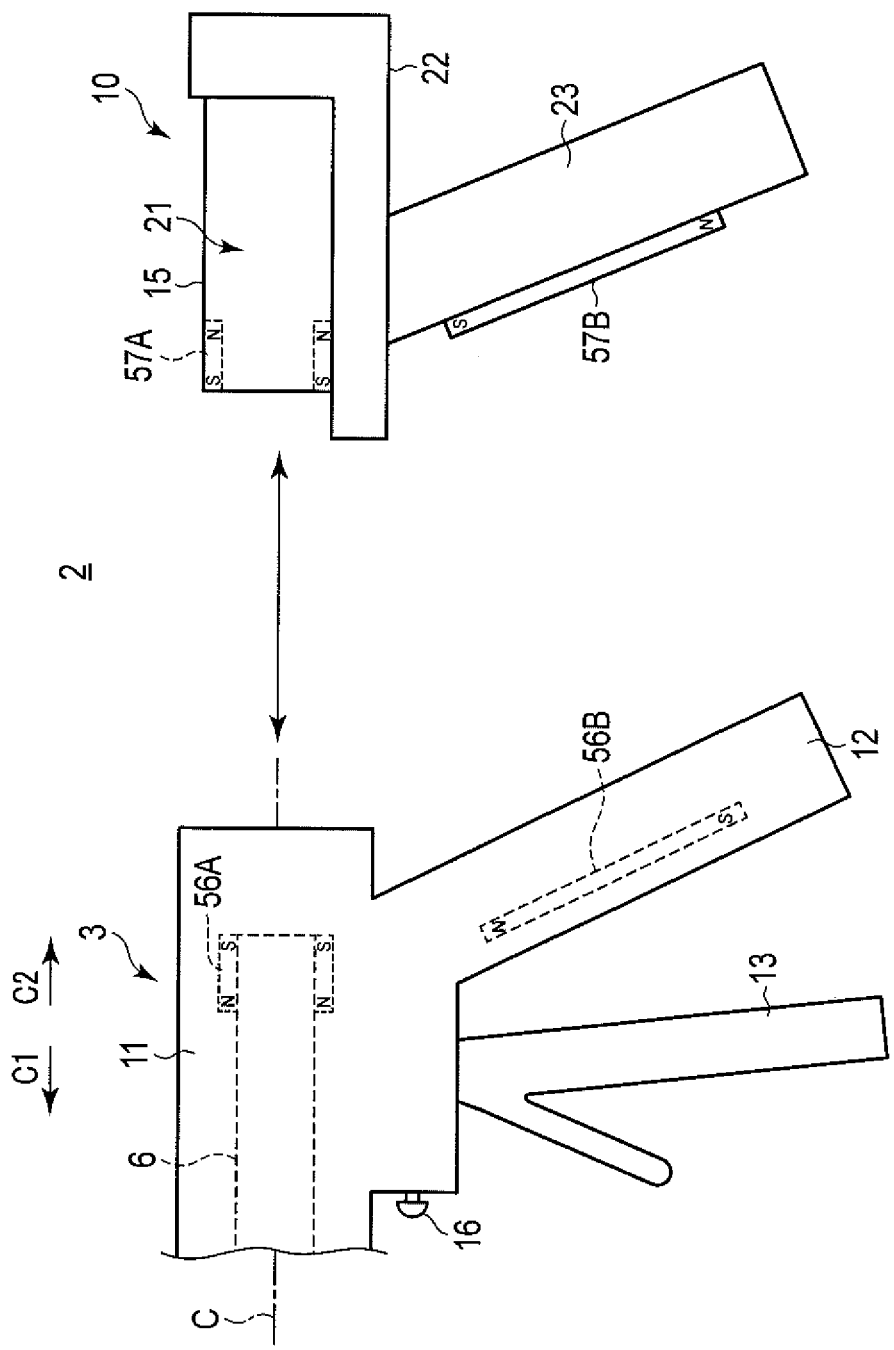
FIG. 9 is a schematic diagram illustrating the configuration of the handle assembly and the drive assembly according to the third modification in a state where the drive assembly is separated from the handle assembly.

In the third modification illustrated in FIG. 9, a magnet (a first magnet) 56A is arranged in the proximal portion of the sheath 6, and a magnet (a first magnet) 56B is arranged in the stationary handle 12. A magnet (a second magnet) 57A is arranged in the transducer case 25, and a magnet (a second magnet) 57B is arranged in the battery unit 23. In the ultrasonic treatment instrument 2 in which the drive assembly 10 is coupled to the handle assembly 3, the magnet 57A is arranged opposite to the magnet 56A, and the magnet 57B is arranged opposite to the magnet 56B. Furthermore, magnetic attraction acts between the magnet 56A and the magnet 57A, and between the magnet 56B and the magnet 57B. Thus, when coupling the drive assembly 10 to the handle assembly 3 to which the probe 5 and the sheath 6 are attached, the magnetic attraction between the first magnet (56A, 56B) on the handle assembly 3 side and the second magnet (57A, 57B) on the drive assembly 20 side makes it easy to assemble the ultrasonic treatment instrument 2. By using the magnetic attraction between the first magnet (56A, 56B) and the second magnet (57A, 57B), the drive assembly 10 can be easily coupled to the handle assembly 3 in a dark place, such as an operating room, etc. during an operation, for example.

In another modification, in addition to the above-described treatment using the ultrasonic vibration, bipolar treatment may be performed using the jaw 7 and the probe treatment section 8 as electrodes of a high-frequency electric power. In this case, a circuit for converting a direct-current power output from the battery 37 into a high-frequency electric power is provided in the drive control section 35. Furthermore, the drive control section 35 supplies the jaw 7 and the probe treatment section 8 with the high-frequency electric power. During such bipolar treatment, a high-frequency current is applied to a target for treatment which is gripped between the jaw 7 and the probe treatment section 8 to coagulate the treated target.

In the above-described embodiments, etc., the handle assembly (3) of the ultrasonic treatment instrument (2) includes a case (11) inside which the proximal portion of a probe (5) is located, and a movable handle (13) which is extended from the case (11) in a direction intersecting the longitudinal axis and which is movably attached to the case (11). The drive assembly (10) includes a vibration generation section (26) which generates an ultrasonic vibration by being driven, a battery (37) which outputs an electric power, and a drive control section (35) controlling the drive of the vibration generation section using the electric power from the battery (37). By integrally and detachably coupling the drive assembly (10) to the handle assembly (3), the vibration generation section (26) is connected to the probe (6) in the inside of the case (11) from the proximal direction (C2) side. While the drive assembly (10) is coupled to the handle assembly (3), the opposite extended portion (47) is extended from the case (11) in a state where the opposite extended portion (47) is opposed to the movable handle (13) on the proximal direction (C2) side with respect to the movable handle (13), and a space between the opposite extended portion (47) and the movable handle (13) can be opened and closed. While the drive assembly (10) is coupled to the handle assembly (3), the battery (37) is located in the opposite extended section (47).

(Reference Examples)

Figure 10:
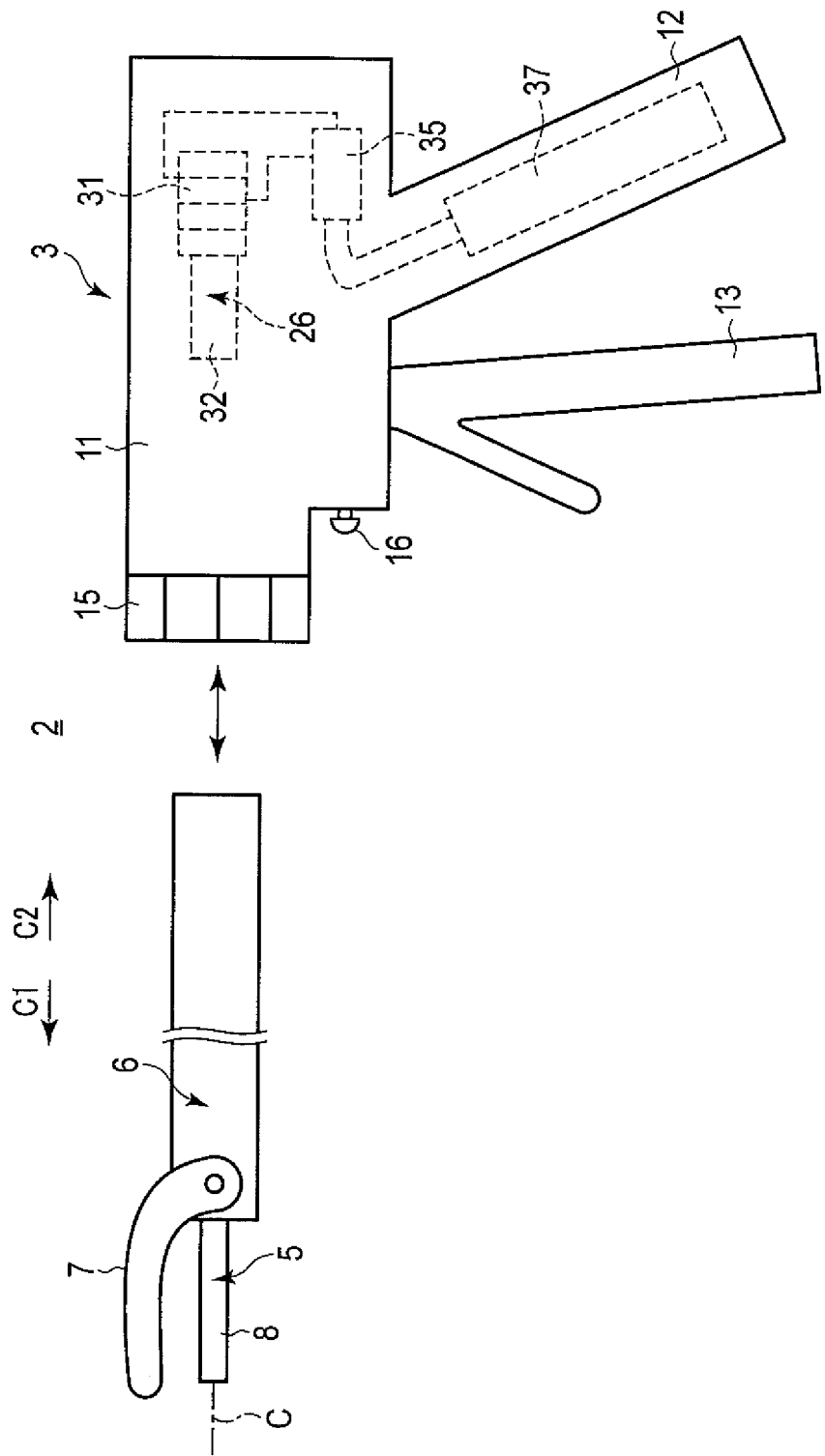
FIG. 10 is a schematic diagram illustrating the configuration of the ultrasonic treatment instrument according to the first reference example in a state where the sheath and the probe are separated from the handle assembly.

The first reference example illustrated in FIG. 10 will be described below. In the present reference example, the probe 5 and the sheath 6 are integrally and detachably coupled to the handle assembly 3. In the held assembly 3, similar to the first embodiment, the case 11, the stationary handle 11, the movable handle 13, the rotating operation knob 15, and energy operation input button 16 are provided. It should be noted, however, that in the present reference example a drive assembly (10) is not provided; instead, the vibration generation section 26 including the ultrasonic transducer 31 and the drive control section 35 that controls the drive of the vibration generation section 26 are provided inside of the case 11. Furthermore, the battery 37 that supplies direct current power to the drive control section 35 is provided inside the stationary handle 12. Thus, in the present reference example, the vibration generation section 26 (ultrasonic vibrator 31), the drive control section 35 and the battery 37 are formed integrated with the handle assembly 3.

In the present reference example, the sheath 6 is coupled to the handle assembly 3 by inserting the sheath 6 into the inside of the rotating operation knob 15 and the inside of the case 11 from the distal direction side. The vibration generation section 26 is connected to the probe 5 on the proximal direction side in the inside of the case 11 by inserting the probe 5 into the inside of the rotating operation knob 15 and the inside of the case 11 from the distal direction side. Thus, an ultrasonic vibration generated at the vibration generation section 26 (ultrasonic transducer 31) can be transmitted to the probe treatment section 8 via the probe 5.

Because of the above-described configuration, the ultrasonic treatment instrument 2, in which the ultrasonic vibration can be transmitted to the probe treatment section 8, can be assembled by coupling the probe 5 and the sheath 6 integrally to the handle assembly 3. In other words, the probe 5 is connected to the vibration generation section 26 (ultrasonic transducer 31) only by coupling the probe 5 and the sheath 6 to the handle assembly 3. Thus, simplification of the configuration for assembling the ultrasonic treatment instrument 2 can be realized, and the ultrasonic treatment tool 2 can be easily assembled.

Furthermore, various types of probes 5 having different shapes of the probe treatment sections 8 with respect to each other, for example, can be coupled to the handle assembly 3. Accordingly, it is possible to use the same handle assembly 3 for various ultrasonic treatments only by changing the type of the probe 5 to be coupled to the handle assembly 3 in accordance with a type of treatment and a purpose of use, etc.

When an operation is finished, the probe 5 and the sheath 6 are detached from the handle assembly 3, and the probe 5, the sheath 6, and the jaw 7 are discarded. On the other hand, the handle assembly 3 including expensive piezoelectric elements 33 (vibration generation section 26) and the battery 37 are sterilized for reuse. Thus, it is possible to integrally separate the reusable members from the members to be discarded by detaching the probe 5 and the sheath 6 from the handle assembly 3.

Figure 11:
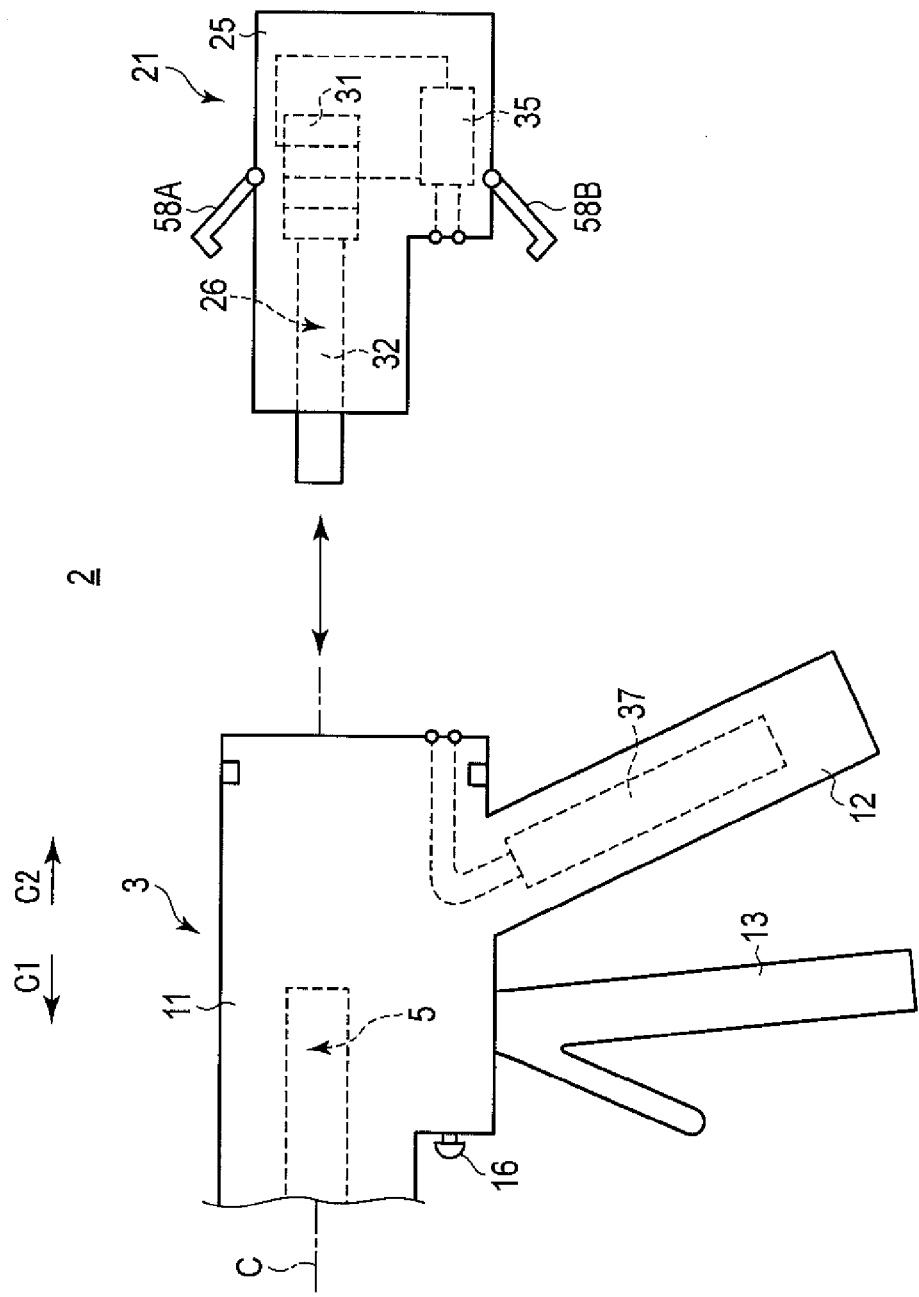
FIG. 11 is a schematic diagram illustrating the configuration of the handle assembly and the transducer unit according to the second reference example in a state where the transducer unit is separated from the handle assembly.
Figure 12:
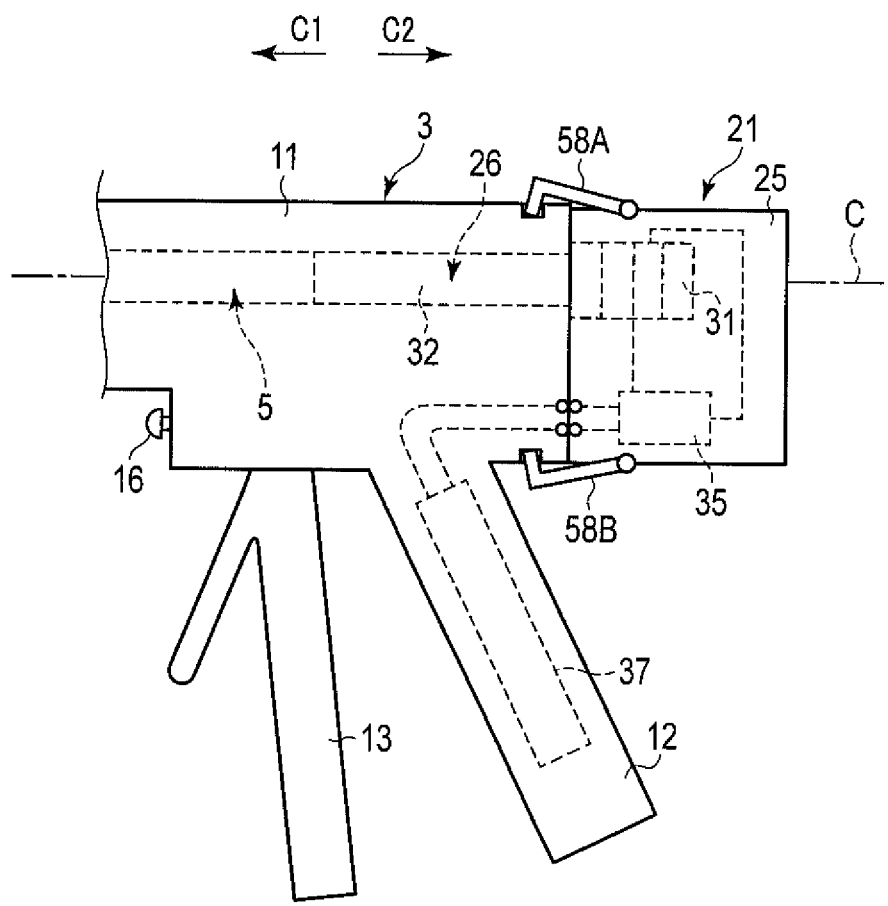
FIG. 12 is a schematic diagram illustrating the configuration of the handle assembly and the transducer unit according to the second reference example in a state where the transducer unit is coupled to the handle assembly.

The second reference examples shown in FIGS. 11 and 12 are described. In the present reference example, the transducer unit (generator unit 21) is detachably attached to the handle assembly 3 to which the probe 5 and the sheath 6 are attached. The transducer unit 21 includes the transducer case 25, and the vibration generation section 26 (ultrasonic transducer 31) generating an ultrasonic vibration and the drive control section 35 controlling the drive of the vibration generation section 26 are provided inside the vibrator case 25. In the handle assembly 3, similar to the first embodiment, the case 11, the stationary handle 12, the movable handle 13, the rotating operation knob 15, and the energy operation input button 16 are provided. Furthermore, the battery 37 for supplying a direct current to the drive control section 35 is provided inside the stationary handle 12.

Since the transducer unit 21 is coupled to the handle assembly 3, the transducer case 25 is coupled to the sheath 6 on the proximal direction side in the inside of the case 11. Furthermore, the vibration generation section 26 is connected to the probe 5 from the proximal direction side in the inside of the case 11. In such case, the distal end of the vibration generation section 26 (the distal end of the horn member 32) and the proximal end of the probe 5 are abutted. Therefore, the ultrasonic vibration generated at the vibration generation section 26 (ultrasonic transducer 31) can be transmitted to the probe 5.

In the present reference example, locking members (fastening fixtures) 58A and 58B are rotatably attached to the transducer case 25. The locking members 58A and 58B are formed in approximately an L shape. In the present reference example, while the distal end of the vibration generation section 26 and the proximal end of the probe 5 are abutted, each of the locking members 58A and 58B is rotated to the position where each of them lock in the case 11 of the handle assembly 3. By locking the locking members 58A and 58B in the case 11, the vibration generation section 26 and the probe 5 press down against each other at the position where the vibration generation section 26 and the probe 5 are abutted. Due to this, the abutting status of the distal end of the vibration generation section 216 and the proximal end of the probe 5 can be maintained. In other words, the status of being able to transmit the ultrasonic vibration from the vibration generation section 26 to the probe 5 can be maintained.

When the transducer unit 21 is detached from the handle assembly 3, each of the locking members 58A and 58B is rotated from the position where each of them lock in the case 11. Thus, it is possible to separate the vibration generation section 26 from the probe 5.

For example, in a configuration in which the proximal portion of the probe (5) and the distal portion of the vibration generation section (26) are threadedly engaged, it is necessary to threadedly engage the probe (5) and the vibration generation section (26) using a torque wrench. Thus, it is necessary to form a part to which fastening torque is applied by the torque wrench and a mechanism, etc. to adjust the fastening torque; thus, a configuration for connecting the vibration generation section (26) to the probe (5) would become complicated.

In contrast, in the present reference example, the abutting status of the distal end of the vibration generation section 26 and the proximal end of the probe 5 can be maintained only by locking each of the locking members 58A and 58B in the case 11 of the handle assembly 3. Accordingly, the vibration generation section 26 can be connected to the probe 5 with a simple configuration.

In another reference example, locking members (58A, 58B) are not provided in the transducer case 25, but are rotatably attached to the case 11 of the handle assembly 3. In this case, while the distal end of the vibration generation section 26 and the proximal end of the probe 5 are abutted, the locking members (58A, 58B) are rotated to the position where they lock in the transducer case 25 of the transducer unit 21. Similar to the second reference example, the abutting status of the distal end of the vibration generation section 26 and the proximal end of the probe 5 can be maintained by locking the locking members (58A, 58B) in the transducer case 25.

In the following, characteristic matters will be appended.

Note (Supplemental Matter 1)

An ultrasonic treatment instrument comprising:

a probe which has a distal portion and a proximal portion, is extended along a longitudinal axis C, and is configured to transmit an ultrasonic vibration;

a handle assembly including a case inside which the proximal portion of the probe is located, and a movable handle which is extended from the case in a direction intersecting the longitudinal axis and which is movably attached to the case; and a drive assembly including a vibration generation section which is configured to generate the ultrasonic vibration by being driven, a battery which is configured to output an electric power, and a drive control section which is configured to control a drive of the vibration generation section using the electric power from the battery, the drive assembly being integrally and detachably coupled to the handle assembly so that the vibration generation section is connected to the probe from a proximal direction side in an inside of the case, so that the battery is extended from the case in a state where the battery is opposed to the movable handle on the proximal direction side with respect to the movable handle, and so that the battery is located in a position where the movable handle can close and open.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic instrument comprising:
   a probe which has a distal portion and a proximal portion, is extended along a longitudinal axis C, and is configured to transmit an ultrasonic vibration;
   a handle assembly including a case inside which the proximal portion of the probe is located, and a movable handle which is extended from the case in a direction intersecting the longitudinal axis and which is movably attached to the case;
   an opposite extended portion which is extended from the case in a state where the opposite extended portion is opposed to the movable handle on a proximal direction side with respect to the movable handle, a space between the movable handle and the opposite extended portion being able to be opened and closed; and
   a drive assembly including a vibration generation section which is configured to generate the ultrasonic vibration by being driven, a transducer case inside which the vibration generating section is provided and which supports the vibration generating section, a supporting member to which the transducer case is fixed, a battery which is fixed to the supporting member on a side opposite to the Vibration generating section and the vibrator case and which is configured to output an electric power, and a drive control section which is provided in the supporting member and which is configured to control a drive of the vibration generation section using the electric power from the battery,
   wherein the vibration generation section is connected to the probe from the proximal direction side in the inside of the case and the battery is located in the opposite extended section by integrally and detachably coupling the drive assembly to the handle assembly and the opposite extended section.

2. The ultrasonic treatment instrument according to claim 1, wherein the handle assembly includes a stationary handle which is fixed to the case, and which forms a part of the opposite extended portion, a storing cavity in which the battery is stored being internally formed in the stationary handle.

3. The ultrasonic treatment instrument according to claim 2,
   wherein an opening of the storing cavity is formed in the stationary handle, the opening being open to the exterior of the stationary handle toward the proximal direction side, and
   the battery is inserted into the storing cavity from the opening by coupling the drive assembly to the handle assembly.

4. The ultrasonic treatment instrument according to claim 3, wherein the handle assembly includes a lid member which covers the opening of the storing cavity by being detachably attached to the stationary handle.

5. The ultrasonic treatment instrument according to claim 1,
   wherein the handle assembly includes a stationary handle which is detachably fixed to the case, and is extended from the case in a state where the stationary handle is opposed to the movable handle on the proximal direction side with respect to the movable handle by being fixed to the case, a space between the stationary handle and the movable handle being able to be opened and closed, and
   a part of the drive assembly forms the opposite extended portion in which the battery is located, by coupling the drive assembly to the handle assembly in which the stationary handle is removed from the case.

6. The ultrasonic treatment instrument according to claim 1,
   wherein an angle between a direction in which the opposite extended portion is extended from the case and a proximal direction is an acute angle, and when the movable handle is most open with respect to the opposite extended portion, an angle between the direction in which the movable handle is extended from the case and the proximal direction is an acute angle.

7. The ultrasonic treatment instrument according to claim 1, wherein the handle assembly includes a switch electrically connected to the drive control section by coupling the drive assembly to the handle assembly.

\* \* \* \* \*